United States Patent
Ghosh et al.

(10) Patent No.: US 9,487,541 B2
(45) Date of Patent: *Nov. 8, 2016

(54) FUSED TRICYCLIC ETHER CARBAMATES AND THEIR USE

(71) Applicants: PURDUE RESEARCH FOUNDATION, West Lafayette, IN (US); NATIONAL UNIVERSITY CORPORATION KUMAMOTO UNIVERSITY, Kumamoto (JP)

(72) Inventors: Arun K. Ghosh, West Lafayette, IN (US); Chun-Xiao Xu, College Station, TX (US); Hiroaki Mitsuya, Kumamoto (JP); Garth Parham, Largo, FL (US)

(73) Assignees: Purdue Research Foundation, West Lafayette, IN (US); National University Corporation Kumamoto University, Kumamoto (JP)

( * ) Notice: Subject to any disclaimer, the term of this patent is extended or adjusted under 35 U.S.C. 154(b) by 86 days.

This patent is subject to a terminal disclaimer.

(21) Appl. No.: 14/048,487

(22) Filed: Oct. 8, 2013

(65) Prior Publication Data

US 2014/0179754 A1    Jun. 26, 2014

Related U.S. Application Data

(63) Continuation of application No. 13/819,141, filed as application No. PCT/US2011/050393 on Sep. 2, 2011, now Pat. No. 8,563,597.

(60) Provisional application No. 61/379,414, filed on Sep. 2, 2010.

(51) Int. Cl.

| *A61K 31/38* | (2006.01) |
|---|---|
| *A61K 31/35* | (2006.01) |
| *A61K 31/34* | (2006.01) |
| *C07D 307/92* | (2006.01) |
| *C07D 495/14* | (2006.01) |
| *C07D 493/04* | (2006.01) |
| *C07D 493/14* | (2006.01) |

(52) U.S. Cl.
CPC ........... *C07D 495/14* (2013.01); *C07D 493/04* (2013.01); *C07D 493/14* (2013.01)

(58) Field of Classification Search
CPC . C07D 493/04; C07D 493/14; C07D 495/14
USPC .......... 514/437, 454, 468; 549/27, 387, 458
See application file for complete search history.

(56) References Cited

U.S. PATENT DOCUMENTS

| 5,627,165 | A | 5/1997 | Glazier |
| 7,763,641 | B2 | 7/2010 | Vendeville et al. |
| 8,563,597 | B2 | 10/2013 | Ghosh et al. |
| 2010/0113582 | A1 | 5/2010 | Ghosh et al. |
| 2013/0158094 | A1 | 6/2013 | Ghosh |

FOREIGN PATENT DOCUMENTS

| EP | 2611295 A1 | 7/2013 |
| JP | 2005-513102 A | 5/2005 |
| JP | 2013536871 A | 9/2013 |
| WO | WO-2008/133734 A2 | 11/2008 |
| WO | WO-2009/105782 A1 | 8/2009 |
| WO | WO-2012031237 A1 | 3/2012 |

OTHER PUBLICATIONS

U.S. Appl. No. 13/819,141, Notice of Allowance mailed Jun. 25, 2013, 12 pgs.
U.S. Appl. No. 13/819,141, Preliminary Amendment filed Feb. 26, 2013, 8 pgs.
European Application Serial No. 11822743.8, Office Action mailed Apr. 17, 2013, 2 pgs.
European Application Serial No. 11822743.8, Response filed Oct. 18, 2013 to Office Action mailed Apr. 17, 2013, 16 pgs.
International Application Serial No. PCT/US2011/050393, International Preliminary Report on Patentability mailed Mar. 14, 2013, 7 pgs.
Tie et al., High Resolution Crystal Structures of HIV-1 Protease with a Potent Non-Peptide Inhibitor (UIC-94017) Active Against Multi-drug-resistant Clinical Strains, J. Mol. Biol., 338:341-352, 2004.
PCT Search Report and Written Opinion for PCT/US2011/050393, completed Jan. 27, 2012.
"European Application Serial No. 11822743.8, Extended European Search Report mailed Jan. 8, 2015", 3 pgs.
Ghosh, Arun K., et al., "Bis-Tetrahydrofuran: A Privileged Ligand for Darunavi and a New Generation of HIV-Protease Inhibitors That Combat Drug-Resistance", ChemMedChem, 1, (2006), 939-950.
Ghosh, Arun K., et al., "Design and Synthesis of Stereochemically Defined Novel Spirocyclic P-2-Ligands for HIV-1 Protease Inhibitors", Org. Lett, 10(22), (2008), 5135-5138.
Ghosh, Arun K., et al., "Probing Multidrug-Resistance and Protein-Ligand Interactions with Oxatricyclic Designed Ligands in HIV-1 Protease Inhibitors", ChemMedChem, 5, (2010), 1850-1854.
"European Application Serial No. 11822743.8, Office Action mailed Jan. 27, 2015", 1 pg.
"European Application Serial No. 11822743.8, Response filed Jun. 28, 2015 to Office Action mailed Jan. 27, 2015", 13 pgs.
"Japanese Application Serial No. 2013-527348, Office Action mailed Jul. 14, 2015", (w/ English Translation), 6 pgs.

*Primary Examiner* — My-Chau T Tran
(74) *Attorney, Agent, or Firm* — Schwegman Lundberg & Woessner, P.A.

(57) ABSTRACT

Tricylic ether carbamates that inhibit HIV proteolytic enzymes and processes for preparing the compounds are describes. Methods of using the disclosed compounds for treating patients infected with HIV are also described.

20 Claims, No Drawings

FUSED TRICYCLIC ETHER CARBAMATES AND THEIR USE

CROSS-REFERENCE TO RELATED APPLICATIONS

This application is a continuation of application Ser. No. 13/819,141, filed Feb. 26, 2013, which is the national stage entry under 35 USC §371(b) of International Application No. PCT/US2011/050393, filed Sep. 2, 2011, which claims priority under 35 U.S.C. §119(e) to U.S. Provisional Application Ser. No. 61/379,414 filed on Sep. 2, 2010, the entire disclosures of which are incorporated herein by reference.

GOVERNMENT RIGHTS

This invention was made with government support under GM053386 awarded by the National Institutes of Health. The government has certain rights in the invention.

TECHNICAL FIELD

This invention relates to compounds that inhibit HIV proteolytic enzymes and processes for preparing the compounds. The invention also relates to methods of using the disclosed compounds for treating patients infected with HIV.

BACKGROUND AND SUMMARY

The AIDS epidemic is one of the most challenging problems in medicine in the 21st century. A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the extensive post-translational processing of precursor polyproteins by a vitally encoded protease to generate mature vital proteins required for virus assembly and function. Inhibition of this processing prevents the production of normally infectious virus. It has been previously demonstrated that genetic inactivation of the HIV encoded protease resulted in the production of immature, non-infectious virus particles. These results indicate that inhibition of the HIV protease represents a viable method for the treatment of AIDS and the prevention or treatment of infection by HIV.

Among many strategies to combat this disease, highly active antiretroviral therapy (HAART) with HIV protease inhibitors (PIs) in combination with reverse transcriptase inhibitors (RTIs) continues to be the first line treatment for control of HIV infection. This treatment regimen has definitely improved quality of life, enhanced HIV management, and halted the progression of the disease. However, despite these impressive successes, there remain many challenges to treating this devastating disease, including decreasing both the toxicity of and complexity of these treatment regimens. In addition, there is a growing population of patients that are developing multi-drug resistant strains of HIV, and there is ample evidence that these strains can be further transmitted.

HAART has had a major impact on the AIDS epidemic in industrially advanced nations; however, eradication of human immunodeficiency virus type 1 (HIV 1) appears to be currently unachieved, in part due to the viral reservoirs remaining in blood and infected tissues. The limitation of antiviral therapy of AIDS is also exacerbated by complicated regimens, the development of drug-resistant HIV-1 variants, and a number of inherent adverse effects. However, a number of challenges have nonetheless been encountered in bringing about the optimal benefits of the currently available therapeutics of AIDS and HIV-1 infection to individuals receiving HAART. They include (i) drug-related toxicities; (ii) partial restoration of immunologic functions once individuals developed AIDS; (iii) development of various cancers as a consequence of survival prolongation; (iv) flame-up of inflammation in individuals receiving HAART or immune re-construction syndrome (IRS); and (v) increased cost of antiviral therapy. Such limitations of HAART are exacerbated by the development of drug-resistant HIV-1 variants.

Efforts to counter the development of resistance with new compounds have been recently reported (Ghosh A K, et al., Bioorg. Med. Chem. Lett. 1998; Ghosh A K, et al., Farmaco 2001; Ghosh A K, et al., Chem Med Chem, 2006; Yoshimura K, et al., J. Virol. 2002; Koh Y, Nakata H, Maeda K., Antimicrob Agents Chemother, 2003). The FDA approved Darunavir on Jun. 23, 2006; on Oct. 21, 2008, FDA granted traditional approval to Prezista (darunavir), co-administered with ritonavir and with other antiretroviral agents, for the treatment of HIV-1 infection in treatment-experienced adult patients. In addition to the traditional approval, a new dosing regimen for treatment-naïve patients was approved (Tie Y, et al., Proteins 2007; Kovalevsky A Y, et al., J. Med. Chem. 2006; Ghosh A K, Chapsal B D, Weber I T, Mitsuya H., Acc. Chem. Res. 2008-; Ghosh A K, et al., J. Med. Chem. 2006; Ghosh A K, et al., J. Med. Chem. 2009; Ghosh A K, Chen Y., Tetrahedron Lett., 1995). One of the PIs, darunavir (DRV), was first approved for HIV/AIDS patients harboring drug-resistant HIV that do not respond to other antiretroviral drugs. Recently, DRV has received full approval for all HIV/AIDS patients including children infected with HIV-1. DRV incorporates a stereochemically defined fused bis-tetrahydrofuran (bis-THF) as the P2-ligand. Each of the documents cited herein is incorporated herein by reference. Inhibition of HIV-1 protease has been documented as an effective strategy for the treatment of HIV/AIDS.

Herein described are potent inhibitors of HIV protease, including against various multidrug-resistant HIV-1 variants. In one embodiment, inhibitors described herein show nearly a 10-fold inhibition improvement over Darunavir (DRV). In another embodiment, inhibitors described herein also potently block protease dimerization by at least a factor of 10-fold compared to DRV.

The invention described herein includes novel compounds and compositions for treating patients in need of relief from HIV, AIDS, and AIDS-related diseases. In addition, the invention described herein includes methods for treating HIV, AIDS, and AIDS-related diseases using the compounds described herein as well as known compounds that heretofore have not been used or described as being useful in the treatment of such diseases.

In an embodiment of the invention, a compound having the formula

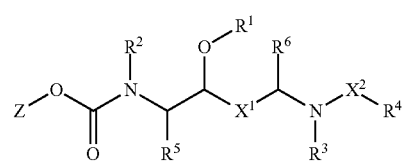

or a pharmaceutically acceptable salt, isomer, mixture of isomers, crystalline form, non crystalline form, hydrate, or solvate thereof; wherein $X^1$ is a bond or optionally substituted alkylene;

$X^2$ is a bond, C(O), S(O), S(O)$_2$, optionally substituted amino, or optionally substituted alkylene;

$R^1$ and $R^2$ are in each instance independently selected from the group consisting of hydrogen, P(O)(OR)$_2$ and a prodrug forming group, where R is independently selected in each instance from hydrogen or alkyl;

$R^3$ is sulfonyl, acyl, amino, alkyl, heteroalkyl, cycloalkyl, cycloheteroalkyl, aryl, arylalkyl, heteroaryl, or heteroarylalkyl, each of which is optionally substituted;

$R^4$ is hydrogen, halogen, —OH, or —NO$_2$, or $R^4$ is amino, alkoxyl, sulfonyl, acyl, alkyl, heteroalkyl, cycloalkyl, cycloheteroalkyl, aryl, and heteroaryl, each of which is optionally substituted; or $R^3$, $R^4$, $X^2$ and the attached nitrogen form an optionally substituted heterocyclyl;

$R^5$ and $R^6$ are independently in each instance hydrogen or selected from the group consisting of alkyl, heteroalkyl, cycloalkyl, heterocycloalkyl, aryl, arylalkyl, heteroaryl, and heteroarylalkyl, each of which is optionally substituted;

Z is

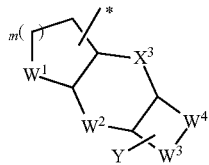

wherein * indicates the point of attachment; m is 0, 1, or 2;

$W^1$ and $W^2$ are in each instance independently selected from the group consisting of optionally substituted alkylene, alkyleneoxy, alkyleneamino, alkylenethio, alkylenesulfoxyl, and alkylenesulfonyl;

$W^3$ and $W^4$ are in each instance independently selected from the group consisting of amino, oxygen, alkylene, alkyleneoxy, alkyleneamino, and heteroalkylene, wherein at least one of $W^1$ or $W^2$ is oxygen, and wherein when one of $W^1$ or $W^2$ is optionally substituted methylene, at least one of $W^3$ or $W^4$ is oxygen or alkyleneoxy, and wherein Z does not include a peroxide bond, a sulfenate bond, or a sulfenamide bond;

$X^3$ is a bond or optionally substituted methylene; and

Y is hydrogen, hydroxyl, or carbonyl, or amino, acyl, sulfonyl, alkyl, or heteroalkyl, each of which is optionally substituted is described.

In another embodiment

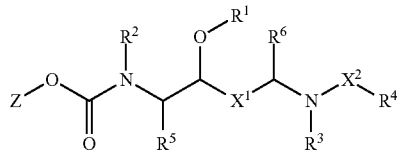

or a pharmaceutically acceptable salt, isomer, mixture of isomers, crystalline form, non crystalline form, hydrate, or solvate thereof; wherein $X^1$ is a bond or optionally substituted alkylene;

$X^2$ is a bond, C(O), S(O), S(O)$_2$, optionally substituted amino, or optionally substituted alkylene;

$R^1$ and $R^2$ are in each instance independently selected from the group consisting of hydrogen, P(O)(OR)$_2$ and a prodrug forming group, where R is independently selected in each instance from hydrogen or alkyl;

$R^3$ is sulfonyl, acyl, amino, alkyl, heteroalkyl, cycloalkyl, cycloheteroalkyl, aryl, arylalkyl, heteroaryl, or heteroarylalkyl, each of which is optionally substituted;

$R^4$ is hydrogen, halogen, —OH, or —NO$_2$, or $R^4$ is amino, alkoxyl, sulfonyl, acyl, alkyl, heteroalkyl, cycloalkyl, cycloheteroalkyl, aryl, and heteroaryl, each of which is optionally substituted; or $R^3$, $R^4$, $X^2$ and the attached nitrogen form an optionally substituted heterocyclyl;

$R^5$ and $R^6$ are independently in each instance hydrogen or selected from the group consisting of alkyl, heteroalkyl, cycloalkyl, heterocycloalkyl, aryl, arylalkyl, heteroaryl, and heteroarylalkyl, each of which is optionally substituted;

Z is

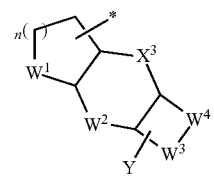

wherein * indicates the point of attachment; n is 1, 2, or 3;

$W^1$ and $W^2$ are in each instance independently selected from the group consisting of optionally substituted methylene, oxygen, and amino;

$W^3$ and $W^4$ are in each instance independently selected from the group consisting of amino, oxygen, alkylene, and heteroalkylene, wherein at least one of $W^1$ or $W^2$ is oxygen, and wherein when one of $W^1$ or $W^2$ is optionally substituted methylene, at least one of $W^3$ or $W^4$ is oxygen, and wherein Z does not include a peroxide bond, a sulfenate bond, or a sulfenamide bond;

$X^3$ is a bond or optionally substituted methylene; and

Y is hydrogen, hydroxyl, or carbonyl, or amino, acyl, sulfonyl, alkyl, or heteroalkyl, each of which is optionally substituted is described.

In another embodiment, a pharmaceutical composition comprising a therapeutically effective amount of one or more of the compounds described herein for treating HIV infection is described.

In another embodiment, compounds described are used in the treatment of HIV, AIDS, and AIDS-related diseases. Also described herein is a method for treating a patient in need of relieve of an HIV infection, the method comprising the step of administering to a patient in need of relief from the HIV infection a therapeutically effective amount of one or more compounds of any of the compounds or the compositions described herein.

In another embodiment, described herein is the synthesis of a series of inhibitors for HIV-1 protease that incorporate conformationally constrained and stereochemically defined tris-tetrahydrofuran derivatives as the P2-ligands. These inhibitors have shown marked enzyme-inhibitory and antiviral potency. A number of these inhibitors are very potent against multi-drug resistant HIV-1 variants.

DETAILED DESCRIPTION

Embodiments of the invention are further described by the following enumerated clauses:

0. A compound having the formula

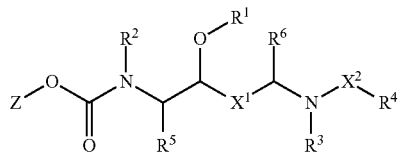

or a pharmaceutically acceptable salt, isomer, mixture of isomers, crystalline form, non crystalline form, hydrate, or solvate thereof; wherein $X^1$ is a bond or optionally substituted alkylene;

$X^2$ is a bond, C(O), S(O), S(O)$_2$, optionally substituted amino, or optionally substituted alkylene;

$R^1$ and $R^2$ are in each instance independently selected from the group consisting of hydrogen, P(O)(OR)$_2$, and a prodrug forming group, where R is independently selected in each instance from hydrogen or alkyl;

$R^3$ is sulfonyl, acyl, amino, alkyl, heteroalkyl, cycloalkyl, cycloheteroalkyl, aryl, arylalkyl, heteroaryl, or heteroarylalkyl, each of which is optionally substituted;

$R^4$ is hydrogen, halogen, —OH, or —NO$_2$, or $R^4$ is amino, alkoxyl, sulfonyl, acyl, alkyl, heteroalkyl, cycloalkyl, cycloheteroalkyl, aryl, and heteroaryl, each of which is optionally substituted; or $R^3$, $R^4$, $X^2$ and the attached nitrogen form an optionally substituted heterocyclyl;

$R^5$ and $R^6$ are independently in each instance hydrogen or selected from the group consisting of alkyl, heteroalkyl, cycloalkyl, heterocycloalkyl, aryl, arylalkyl, heteroaryl, and heteroarylalkyl, each of which is optionally substituted;

Z is

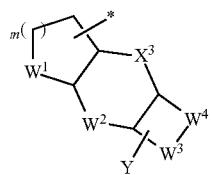

wherein * indicates the point of attachment; m is 0, 1, or 2;

$W^1$ and $W^2$ are in each instance independently selected from the group consisting of optionally substituted alkylene, alkyleneoxy, alkyleneamino, alkylenethio, alkylenesulfoxyl, and alkylenesulfonyl;

$W^3$ and $W^4$ are in each instance independently selected from the group consisting of amino, oxygen, alkylene, alkyleneoxy, alkyleneamino, and heteroalkylene, wherein at least one of $W^1$ or $W^2$ is oxygen, and wherein when one of $W^1$ or $W^2$ is optionally substituted methylene, at least one of $W^3$ or $W^4$ is oxygen or alkyleneoxy, and wherein Z does not include a peroxide bond, a sulfenate bond, or a sulfenamide bond;

$X^3$ is a bond or optionally substituted methylene; and

Y is hydrogen, hydroxyl, or carbonyl, or amino, acyl, sulfonyl, alkyl, or heteroalkyl, each of which is optionally substituted is described.

1. A compound having the formula

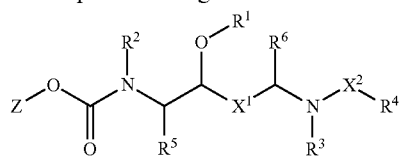

or a pharmaceutically acceptable salt, isomer, mixture of isomers, crystalline form, non crystalline form, hydrate, or solvate thereof; wherein $X^1$ is a bond or optionally substituted alkylene;

$X^2$ is a bond, C(O), S(O), S(O)$_2$, optionally substituted amino, or optionally substituted alkylene;

$R^1$ and $R^2$ are in each instance independently selected from the group consisting of hydrogen, P(O)(OR)$_2$ and a prodrug forming group, where R is independently selected in each instance from hydrogen or alkyl;

$R^3$ is sulfonyl, acyl, amino, alkyl, heteroalkyl, cycloalkyl, cycloheteroalkyl, aryl, arylalkyl, heteroaryl, or heteroarylalkyl, each of which is optionally substituted;

$R^4$ is hydrogen, halogen, —OH, or —NO$_2$, or $R^4$ is amino, alkoxyl, sulfonyl, acyl, alkyl, heteroalkyl, cycloalkyl, cycloheteroalkyl, aryl, and heteroaryl, each of which is optionally substituted; or $R^3$, $R^4$, $X^2$ and the attached nitrogen form an optionally substituted heterocyclyl;

$R^5$ and $R^6$ are independently in each instance hydrogen or selected from the group consisting of alkyl, heteroalkyl, cycloalkyl, heterocycloalkyl, aryl, arylalkyl, heteroaryl, and heteroarylalkyl, each of which is optionally substituted;

Z is

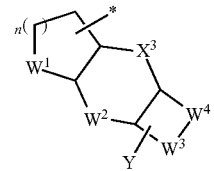

wherein * indicates the point of attachment; n is 1, 2, or 3;

$W^1$ and $W^2$ are in each instance independently selected from the group consisting of optionally substituted methylene, oxygen, and amino;

$W^3$ and $W^4$ are in each instance independently selected from the group consisting of amino, oxygen, alkylene, and heteroalkylene, wherein at least one of $W^1$ or $W^2$ is oxygen, and wherein when one of $W^1$ or $W^2$ is optionally substituted methylene, at least one of $W^3$ or $W^4$ is oxygen, and wherein Z does not include a peroxide bond, a sulfenate bond, or a sulfenamide bond;

$X^3$ is a bond or optionally substituted methylene; and

Y is hydrogen, hydroxyl, or carbonyl, or amino, acyl, sulfonyl, alkyl, or heteroalkyl, each of which is optionally substituted.

2. The compound of clause 1 wherein Z is

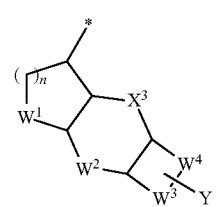

wherein * indicates the point of attachment. 3. The compound of clause 1 or 2 wherein Z is

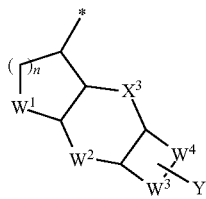

wherein $W^2$ is an oxygen; and * indicates the point of attachment. 4. The compound of any one of the preceding clauses wherein $X^3$ is a bond. 5. The compound of any one of the preceding clauses wherein n is 1 or 2. 6. The compound of any one of the preceding clauses wherein $W^4$ is optionally substituted ethylene or propylene. 7. The compound of any one of the preceding clauses wherein n is 1. 8. The compound of any one of the preceding clauses wherein $W^4$ is ethylene. 9. The compound of any one of the preceding clauses wherein Y is hydrogen. 10. The compound of any one of the preceding clauses wherein $W^1$, $W^2$, and $W^3$ are oxygen. 11. The compound of any one of the preceding clauses wherein Z is

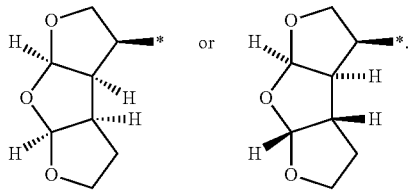

11.1 The compound of any one of the preceding clauses wherein Z is

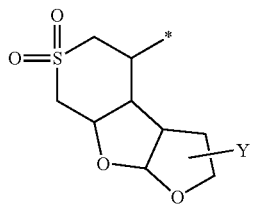

11.2 The compound of any one of the preceding clauses wherein Z is

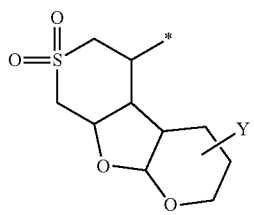

12. The compound of any one of the preceding clauses wherein $R^1$ and $R^2$ are each hydrogen. 13. The compound of any one of the preceding clauses wherein $R^5$ is optionally substituted arylalkyl. 14. The compound of any one of the preceding clauses wherein $X^1$ is a bond and $R^6$ is hydrogen. 15. The compound of any one of the preceding clauses wherein $X^2$ is $S(O)_2$ and $R^4$ is optionally substituted aryl. 16. The compound of any one of the preceding clauses wherein $R^3$ is iso-butyl. 17. The compound of any one of the preceding clauses wherein $X^2$ is NR, where R is hydrogen or alkyl. 18. The compound of any one of the preceding clauses wherein $X^4$ is arylsulfonyl. 18a. The compound of any one of the preceding clauses wherein $R^3$ is optionally substituted arylalkyl. 18b. The compound of any one of the preceding clauses wherein $W^2$ is oxygen. 18c. The compound of any one of the preceding clauses wherein $W^3$ or W4 is oxygen. 18d. The compound of any one of the preceding clauses wherein $W^2$ and one of $W^3$ or $W^4$ is oxygen. 18e. The compound of any one of the preceding clauses wherein $W^2$ and $W^3$ are oxygen. 18f. The compound of any one of the preceding clauses wherein each of $W^1$, $W^2$, and W3 is oxygen. 18g. The compound of any one of the preceding clauses wherein $W^1$ is optionally substituted methylene. 18h. The compound of any one of the preceding clauses wherein $X^1$ is optionally substituted alkylene; and $R^6$ is aryl or arylalkyl, each of which is optionally substituted. 19. A pharmaceutical composition comprising a therapeutically effective amount of one or more compounds of any one of the preceding clauses for treating HIV infection. 20. The composition of clause 19 further comprising one or more carriers, diluents, or excipients, or a combination thereof. 21. A method for treating a patient in need of relieve of an HIV infection, the method comprising the step of administering to a patient in need of relief from the HIV infection a therapeutically effective amount of one or more compounds of any one of clauses 1 to 18h or the composition of clause 19 or 20. 21. The compound of clause 0 or 1 wherein Z is

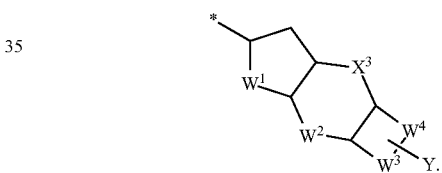

22. The compound of clause 0 or 1 wherein Z is

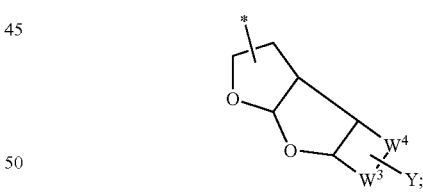

wherein $W^3$ is optionally substituted methylene; and $W^4$ is —$CH_2O$— or —$OCH_2$—.

23. The compound of clause 0 or 1 wherein Z is

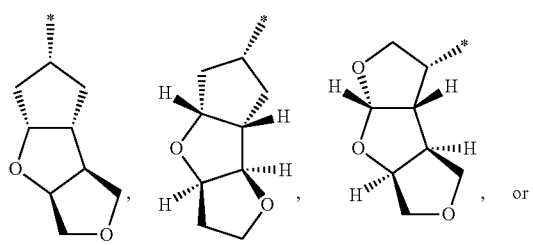

-continued

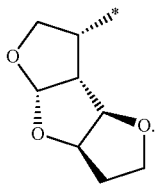

24. The compound of clause 0 or 1 wherein Z is

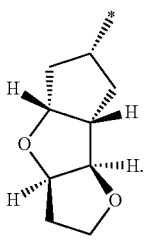

25. The compound of clause 0 or 1 wherein Z is

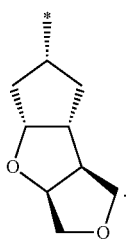 [SMILES: *[C@@H]1C[C@@H]2[C@H]3COC[C@H]3O[C@@H]2C1]

26. The compound of clause 0 or 1 wherein Z is

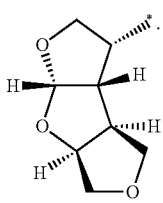 [SMILES: *[C@H]1CO[C@H]2O[C@@H]3COC[C@@H]3[C@H]21]

27. The compound of clause 0 or 1 wherein Z is

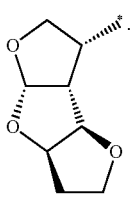

In another embodiment, a compound having the formula

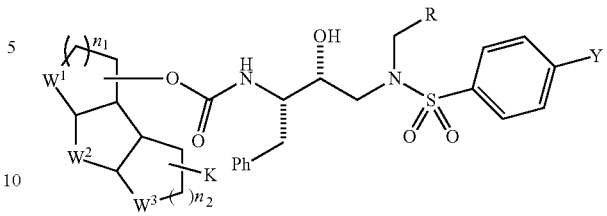

$W^1=W^2=W^3=O$
$W^1=CH_2, W^2=W^3=O$
$W^1=O, W^2=CH_2; W^3=O$
$W^1=W^2=O, W=O, W^3=CH_2$
$n_1=n_2=1, 2, 3$
Y=OMe, $CH_2NH_2$, $NH_2$, other hetero and heteroalkyl groups
R=$CHMe_2$, alkyl, heteroalkyl and the like.
K=OH, $NH_2$, NHMe, NHR, $SO_2$, and the like is described.

In another embodiment, a compound having the formula

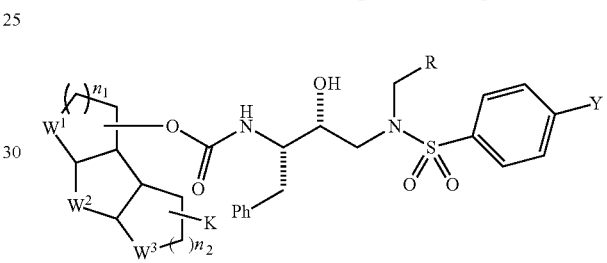

$W^1=W^2=W^3=O$
$W^1=CH_2, W^2=W^3=O$
$W^1=O, W^2=CH_2; W^3=O$
$W^1=W^2=O, W=O, W^3=CH_2$
$n_1=n_2=1, 2, 3$
Y=OMe, $CH_2NH_2$, $NH_2$, other hetero and heteroalkyl groups
R=$CHMe_2$, alkyl, heteroalkyl and the like.
K=OH, $NH_2$, NHMe, NHR, $SO_2$, and the like is described.

In another embodiment, a compound having the formula

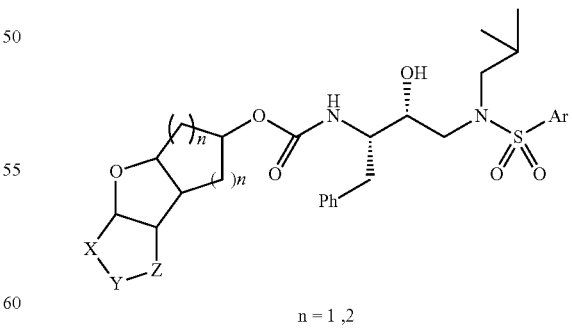

n = 1, 2

X=Y=Z=$CH_2$
X=O, NR, Y=Z=$CH_2$ where R=H, Me, $SO_2Me$, $CO_2Me$, and the like
X=Y=$CH_2$, Z=O, NR
X=Z=$CH_2$, Y=O, NR is described, where Ar=p-PhOMe, p-PhNH2, p-PH—CH2OH, p,m-substituted aromatic, substituted benoxazole, benzoxazole, benzodioxane, benzodioxolane, and the like.

In another embodiment, a compound having the formula

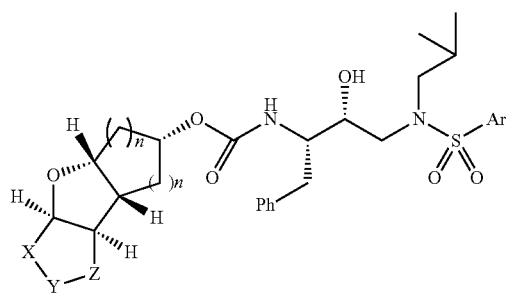

n = 1, 2

$X=Y=Z=CH_2$ $X=O$, NR, $Y=Z=CH_2$ where R=H, Me, $SO_2Me$, $CO_2Me$, and the like $X=Y=CH_2$, $Z=O$, NR $X=Z=CH_2$, $Y=O$, NR is described, where Ar=p-PhOMe, p-PhNH2, p-PH-CH2OH, p,m-substituted aromatic, substituted benoxazole, benzoxazole, benzodioxane, benzodioxolane, and the like.

In one illustrative example, the compounds described herein are prepared by a method comprising one or more, or all, of the steps shown in the following scheme.

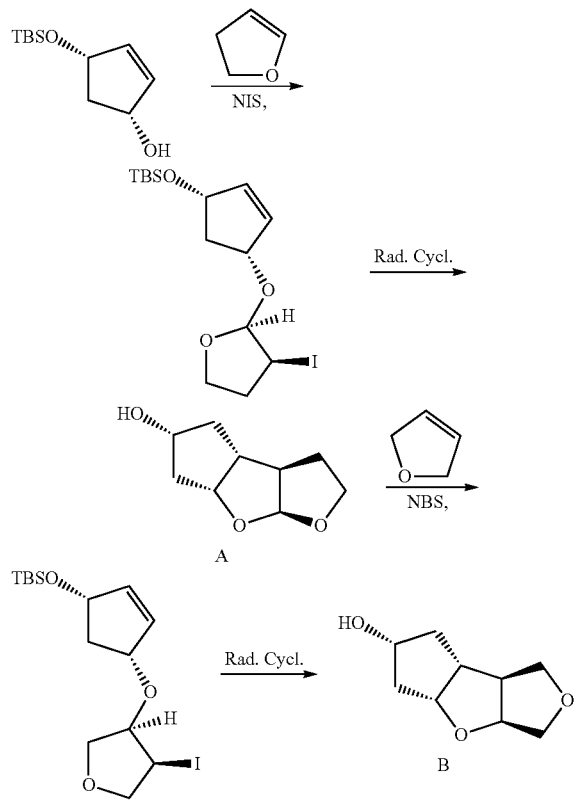

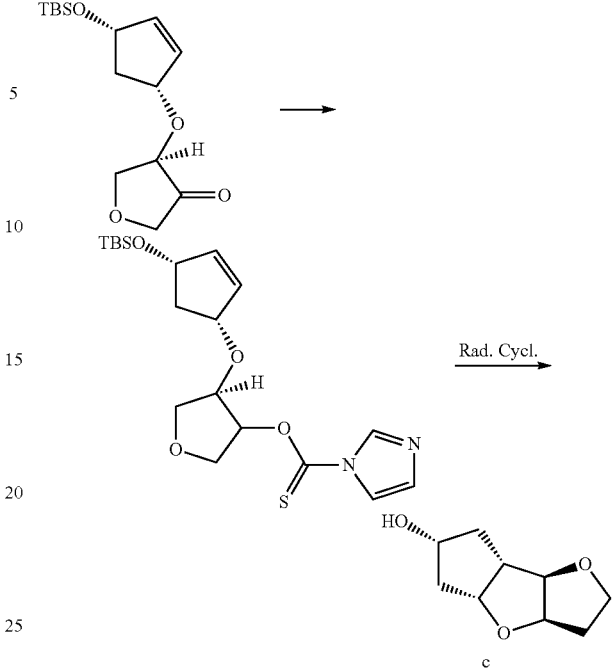

The compounds described herein may contain one or more chiral centers, or may otherwise be capable of existing as multiple stereoisomers. It is to be understood that in one embodiment, the invention described herein is not limited to any particular sterochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

It has been discovered herein that the X-ray structures of both DRV-bound and TMC-126-bound HIV-1 protease complexes revealed extensive protein-ligand hydrogen bonding interactions involving the backbone of HIV-1 protease throughout the active site. In particular, it has also been observed herein that both oxygens of the P2-bis-THF ligand are involved in hydrogen bonding with Asp-29 and Asp-30 backbone NHs. In addition, the bicyclic ligand appears to fill in the hydrophobic pocket at the S2-subsite. Without being bound by theory, it is believed that the P2-bis-THF is responsible for the superior drug-resistance properties of DRV. Without being bound by theory, it is believed herein that to counter drug resistance, the inhibitor design strategies could focus on maximizing inhibitor interactions with the HIV-1 protease active site, particularly to promote extensive hydrogen bond interactions with the protein backbone atoms. It has been discovered herein that enhancing backbone binding leads to PIs that maintain full potency against a panel of multidrug-resistant HIV-1 variants. Based upon examination of the protein-ligand X-ray structure of DRV-bound HIV-1 protease, it has been found that the incorporation of another tetrahydrofuran ring on the bis-THF ligand may provide additional ligand-binding site interactions. Particularly, it appears that ligand oxygens may be able to effectively maintain backbone hydrogen bonding with Asp29 and Asp30 as well as fill in the hydrophobic pocket effectively. Without being bound by theory, it is believed that these interactions may further improve drug-resistance properties of the PIs.

Such oxatricyclic ligand could have a number of possible stereochemical motifs, including a syn-syn-syn (SSS-type) and a syn-anti-syn (SAS-type) isomers. Though both are potent compounds, it is discovered herein that the SAS-type ligand-based PIs have higher affinity, when compared to SSS-isomer. That observation is supported by examination of X-ray structure-based preliminary models suggesting that the SAS-type ligand-based PIs make enhanced interactions in the S2-subsite when compared to SSS-isomer.

In another embodiment, novel oxatricyclic [3(R), 3aS, 4aS, 7aR, 8aS] and [3(R), 3aS, 4aR, 7aS, 8aS]-ligands were designed, synthesized, and incorporated into the (R)-hydroxyethyl sulfonamide isostere. Illustratively, compound 33 exhibits remarkable enzyme inhibitory and antiviral potency. The antiviral activity of 33 against a panel of highly PI-resistant clinical HIV-1 variants in vitro was measured. It was found that 33 effectively suppressed all tested clinical HIV-1 variants that are highly resistant to a number of currently available PIs.

Without being bound by theory, it is believed that successful antiviral drugs exert their virus-specific effects by interacting with viral receptors, virally encoded enzymes, viral structural components, viral genes, or their transcripts without disturbing cellular metabolism or function. However, at present, it is believed that current antiretroviral drugs and agents are unlikely to be completely specific for HIV-1 or to be devoid of toxicity or side effects in the therapy of AIDS. Those issues are of special note because patients with AIDS and its related diseases will have to receive antiretroviral therapy for a long period of time, perhaps for the rest of their lives.

Without being bound by theory, it is also suggested that the compounds described herein may exert their utility by the inhibition of proteases encoded by human immunodeficiency virus (HIV), such as HIV-1. It is appreciated that the compounds described herein may inhibit the homodimer form of the HIV-1 protease, or it may inhibit formation of a functional enzyme, e.g. inhibit dimerization of the protein subunits. The compounds or pharmaceutically acceptable salts thereof, are of value in the prevention of infection by HIV, the treatment of infection by HIV and the treatment of the resulting acquired immune deficiency syndrome (AIDS), either as compounds, pharmaceutically acceptable salts, or pharmaceutical composition ingredients.

It is appreciated that the compounds described herein may be used alone or in combination with other compounds useful for treating such diseases, including those compounds that may operate by the same or different modes of action. Further, it is appreciated that the compounds and compositions described herein may be administered alone or with other compounds and compositions, such as other antivirals, immunomodulators, antibiotics, vaccines, and the like.

As used herein, the term "alkyl" includes a chain of carbon atoms, which is optionally branched. As used herein, the term "alkenyl" and "alkynyl" includes a chain of carbon atoms, which is optionally branched, and includes at least one double bond or triple bond, respectively. It is to be understood that alkynyl may also include one or more double bonds. It is to be further understood that alkyl is advantageously of limited length, including $C_1$-$C_{24}$, $C_1$-$C_{12}$, $C_1$-$C_8$, $C_1$-$C_6$, and $C_1$-$C_4$. It is to be further understood that alkenyl and/or alkynyl may each be advantageously of limited length, including $C_2$-$C_{24}$, $C_2$-$C_{12}$, $C_2$-$C_8$, $C_2$-$C_6$, and $C_2$-$C_4$. It is appreciated herein that shorter alkyl, alkenyl, and/or alkynyl groups may add less lipophilicity to the compound and accordingly will have different pharmacokinetic behavior.

As used herein, the term "cycloalkyl" includes a chain of carbon atoms, which is optionally branched, where at least a portion of the chain in cyclic. It is to be understood that cycloalkylalkyl is a subset of cycloalkyl. It is to be understood that cycloalkyl may be polycyclic. Illustrative cycloalkyl include, but are not limited to, cyclopropyl, cyclopentyl, cyclohexyl, 2-methylcyclopropyl, cyclopentyleth-2-yl, adamantyl, and the like. As used herein, the term "cycloalkenyl" includes a chain of carbon atoms, which is optionally branched, and includes at least one double bond, where at least a portion of the chain in cyclic. It is to be understood that the one or more double bonds may be in the cyclic portion of cycloalkenyl and/or the non-cyclic portion of cycloalkenyl. It is to be understood that cycloalkenylalkyl and cycloalkylalkenyl are each subsets of cycloalkenyl. It is to be understood that cycloalkyl may be polycyclic. Illustrative cycloalkenyl include, but are not limited to, cyclopentenyl, cyclohexylethen-2-yl, cycloheptenylpropenyl, and the like. It is to be further understood that chain forming cycloalkyl and/or cycloalkenyl is advantageously of limited length, including $C_3$-$C_{24}$, $C_3$-$C_{12}$, $C_3$-$C_8$, $C_3$-$C_6$, and $C_5$-$C_6$. It is appreciated herein that shorter alkyl and/or alkenyl chains forming cycloalkyl and/or cycloalkenyl, respectively, may add less lipophilicity to the compound and accordingly will have different pharmacokinetic behavior. As used herein the term "alkylene" refers to a divalent alkyl moiety.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like. As used herein the term "heteroalkylene" refers to a divalent heteroalkyl moiety.

As used herein, the term "aryl" includes monocyclic and polycyclic aromatic groups, including aromatic carbocyclic and aromatic heterocyclic groups, each of which may be optionally substituted. As used herein, the term "carbaryl" includes aromatic carbocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "amino" includes the group $NH_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2N$-alkyl, methylaminoalkyl, ethylaminoalkyl, dimethylaminoalkyl, methylethylaminoalkyl, and the like. Illustratively, acylamino includes acylmethylamino, acylethylamino, and the like.

As used herein, the term "amino and derivatives thereof" includes amino as described herein, and alkylamino, alkenylamino, alkynylamino, heteroalkylamino, heteroalkenylamino, heteroalkynylamino, cycloalkylamino, cycloalkenylamino, cycloheteroalkylamino, cycloheteroalkenylamino, arylamino, arylalkylamino, arylalkenylamino, arylalkynylamino, acylamino, and the like, each of which is optionally substituted. The term "amino derivative" also includes urea, carbamate, and the like.

As used herein, the term "hydroxy and derivatives thereof" includes OH, and alkyloxy, alkenyloxy, alkynyloxy, heteroalkyloxy, heteroalkenyloxy, heteroalkynyloxy, cycloalkyloxy, cycloalkenyloxy, cycloheteroalkyloxy, cycloheteroalkenyloxy, aryloxy, arylalkyloxy, arylalkenyloxy, arylalkynyloxy, acyloxy, and the like, each of which is optionally substituted. The term "hydroxy derivative" also includes carbamate, and the like.

As used herein, the term "thio and derivatives thereof" includes SH, and alkylthio, alkenylthio, alkynylthio, heteroalkylthio, heteroalkenylthio, heteroalkynylthio, cycloalkylthio, cycloalkenylthio, cycloheteroalkylthio, cycloheteroalkenylthio, arylthio, arylalkylthio, arylalkenylthio, arylalkynylthio, acylthio, and the like, each of which is optionally substituted. The term "thio derivative" also includes thiocarbamate, and the like.

As used herein, the term "acyl" includes formyl, and alkylcarbonyl, alkenylcarbonyl, alkynylcarbonyl, heteroalkylcarbonyl, heteroalkenylcarbonyl, heteroalkynylcarbonyl, cycloalkylcarbonyl, cycloalkenylcarbonyl, cycloheteroalkylcarbonyl, cycloheteroalkenylcarbonyl, arylcarbonyl, arylalkylcarbonyl, arylalkenylcarbonyl, arylalkynylcarbonyl, acylcarbonyl, and the like, each of which is optionally substituted.

As used herein, the term "carboxylate and derivatives thereof" includes the group $CO_2H$ and salts thereof, and esters and amides thereof, and CN.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, and/or sulfonic acid is optionally substituted.

As used herein, the term "optionally substituted aryl" includes the replacement of hydrogen atoms with other functional groups on the aryl that is optionally substituted. Such other functional groups illustratively include, but are not limited to, amino, hydroxyl, halo, thiol, alkyl, haloalkyl, heteroalkyl, aryl, arylalkyl, arylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, and/or sulfonic acid is optionally substituted.

Illustrative substituents include, but are not limited to, a radical $—(CH_2)_xZ^X$, where x is an integer from 0-6 and $Z^X$ is selected from halogen, hydroxy, alkanoyloxy, including $C_1$-$C_6$ alkanoyloxy, optionally substituted aroyloxy, alkyl, including $C_1$-$C_6$ alkyl, alkoxy, including $C_1$-$C_6$ alkoxy, cycloalkyl, including $C_3$-$C_8$ cycloalkyl, cycloalkoxy, including $C_3$-$C_8$ cycloalkoxy, alkenyl, including $C_2$-$C_6$ alkenyl, alkynyl, including $C_2$-$C_6$ alkynyl, haloalkyl, including $C_1$-$C_6$ haloalkyl, haloalkoxy, including $C_1$-$C_6$ haloalkoxy, halocycloalkyl, including $C_3$-$C_8$ halocycloalkyl, halocycloalkoxy, including $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl) aminoalkyl, alkylcarbonylaminoalkyl, N—($C_1$-$C_6$ alkyl)alkylcarbonylaminoalkyl, cyano, and nitro; or $Z^X$ is selected from $—CO_2R^4$ and $—CONR^5R^6$, where $R^4$, $R^5$, and $R^6$ are each independently selected in each occurrence from hydrogen, $C_1$-$C_6$ alkyl, and aryl-$C_1$-$C_6$ alkyl.

The term "prodrug" as used herein generally refers to any compound that when administered to a biological system generates a biologically active compound as a result of one or more spontaneous chemical reaction(s), enzyme-catalyzed chemical reaction(s), and/or metabolic chemical reaction(s), or a combination thereof. In vivo, the prodrug is typically acted upon by an enzyme (such as esterases, amidases, phosphatases, and the like), simple biological chemistry, or other process in vivo to liberate or regenerate the more pharmacologically active drug. This activation may occur through the action of an endogenous host enzyme or a non-endogenous enzyme that is administered to the host preceding, following, or during administration of the prodrug. Additional details of prodrug use are described in U.S. Pat. No. 5,627,165; and Pathalk et al., Enzymic protecting group techniques in organic synthesis, Stereosel. Biocatal. 775-797 (2000). It is appreciated that the prodrug is advantageously converted to the original drug as soon as the goal, such as targeted delivery, safety, stability, and the like is achieved, followed by the subsequent rapid elimination of the released remains of the group forming the prodrug.

Prodrugs may be prepared from the compounds described herein by attaching groups that ultimately cleave in vivo to one or more functional groups present on the compound, such as —OH—, —SH, —$CO_2H$, —$NR_2$. Illustrative prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Illustrative esters, also referred to as active esters, include but are not limited to 1-indanyl, N-oxysuccinimide; acyloxyalkyl groups such as acetoxymethyl, pivaloyloxymethyl, β-acetoxyethyl, β-pivaloyloxyethyl, 1-(cyclohexylcarbonyloxy)prop-1-yl, (1-aminoethyl)carbonyloxymethyl, and the like; alkoxycarbonyloxyalkyl groups, such as ethoxycarbonyloxymethyl, α-ethoxycarbonyloxyethyl, β-ethoxycarbonyloxyethyl, and the like; dialkylaminoalkyl groups, including di-lower alkylamino alkyl groups, such as dimethylaminomethyl, dimethylaminoethyl, diethylaminomethyl, diethylaminoethyl, and the like; 2-(alkoxycarbonyl)-2-alkenyl groups such as 2-(isobutoxycarbonyl) pent-2-enyl, 2-(ethoxycarbonyl)but-2-enyl, and the like; and lactone groups such as phthalidyl, dimethoxyphthalidyl, and the like.

Further illustrative prodrugs contain a chemical moiety, such as an amide or phosphorus group functioning to increase solubility and/or stability of the compounds described herein. Further illustrative prodrugs for amino groups include, but are not limited to, $(C_3-C_{20})$alkanoyl; halo-$(C_3-C_{20})$alkanoyl; $(C_3-C_{20})$alkenoyl; $(C_4-C_7)$cycloalkanoyl; $(C_3-C_6)$-cycloalkyl$(C_2-C_{16})$alkanoyl; optionally substituted aroyl, such as unsubstituted aroyl or aroyl substituted by 1 to 3 substituents selected from the group consisting of halogen, cyano, trifluoromethanesulphonyloxy, $(C_1-C_3)$alkyl and $(C_1-C_3)$alkoxy, each of which is optionally further substituted with one or more of 1 to 3 halogen atoms; optionally substituted aryl$(C_2-C_{16})$alkanoyl, such as the aryl radical being unsubstituted or substituted by 1 to 3 substituents selected from the group consisting of halogen, $(C_1-C_3)$alkyl and $(C_1-C_3)$alkoxy, each of which is optionally further substituted with 1 to 3 halogen atoms; and optionally substituted heteroarylalkanoyl having one to three heteroatoms selected from O, S and N in the heteroaryl moiety and 2 to 10 carbon atoms in the alkanoyl moiety, such as the heteroaryl radical being unsubstituted or substituted by 1 to 3 substituents selected from the group consisting of halogen, cyano, trifluoromethanesulphonyloxy, $(C_1-C_3)$alkyl, and $(C_1-C_3)$alkoxy, each of which is optionally further substituted with 1 to 3 halogen atoms. The groups illustrated are exemplary, not exhaustive, and may be prepared by conventional processes.

It is understood that the prodrugs themselves may not possess significant biological activity, but instead undergo one or more spontaneous chemical reaction(s), enzyme-catalyzed chemical reaction(s), and/or metabolic chemical reaction(s), or a combination thereof after administration in vivo to produce the compound described herein that is biologically active or is a precursor of the biologically active compound. However, it is appreciated that in some cases, the prodrug is biologically active. It is also appreciated that prodrugs may often serves to improve drug efficacy or safety through improved oral bioavailability, pharmacodynamic half-life, and the like. Prodrugs also refer to derivatives of the compounds described herein that include groups that simply mask undesirable drug properties or improve drug delivery. For example, one or more compounds described herein may exhibit an undesirable property that is advantageously blocked or minimized may become pharmacological, pharmaceutical, or pharmacokinetic barriers in clinical drug application, such as low oral drug absorption, lack of site specificity, chemical instability, toxicity, and poor patient acceptance (bad taste, odor, pain at injection site, and the like), and others. It is appreciated herein that a prodrug, or other strategy using reversible derivatives, can be useful in the optimization of the clinical application of a drug.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill It is also appreciated that the therapeutically effective amount, whether referring to monotherapy or combination therapy, is advantageously selected with reference to any toxicity, or other undesirable side effect, that might occur during administration of one or more of the compounds described herein. Further, it is appreciated that the co-therapies described herein may allow for the administration of lower doses of compounds that show such toxicity, or other undesirable side effect, where those lower doses are below thresholds of toxicity or lower in the therapeutic window than would otherwise be administered in the absence of a co-therapy.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein. Illustratively, compositions may include one or more carriers, diluents, and/or excipients. The compounds described herein, or compositions containing them, may be formulated in a therapeutically effective amount in any conventional dosage forms appropriate for the methods described herein. The compounds described herein, or compositions containing them, including such formulations, may be administered by a wide variety of conventional routes for the methods described herein, and in a wide variety of dosage formats, utilizing known procedures (see generally, Remington: The Science and Practice of Pharmacy, ($21^{st}$ ed., 2005)).

It is to be understood that in the methods described herein, the individual components of a co-administration or a combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

Illustrative routes of oral administration include tablets, capsules, elixirs, syrups, and the like.

Illustrative routes for parenteral administration include intravenous, intraarterial, intraperitoneal, epidural, intraurethral, intrasternal, intramuscular and subcutaneous, as well as any other art recognized route of parenteral administration. Illustrative means of parenteral administration include needle (including microneedle) injectors, needle-free injectors and infusion techniques, as well as any other means of parenteral administration recognized in the art. Parenteral formulations are typically aqueous solutions which may contain excipients such as salts, carbohydrates and buffering agents (preferably at a pH in the range from about 3 to about 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art. Parenteral administration of a compound is illustratively performed in the form of saline solutions or with the compound incorporated into liposomes. In cases where the compound in itself is not sufficiently soluble to be dissolved, a solubilizer such as ethanol can be applied.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

In making the pharmaceutical compositions of the compounds described herein, a therapeutically effective amount of one or more compounds in any of the various forms described herein may be mixed with one or more excipients, diluted by one or more excipients, or enclosed within such a carrier which can be in the form of a capsule, sachet, paper, or other container. Excipients may serve as a diluent, and can be solid, semi-solid, or liquid materials, which act as a vehicle, carrier or medium for the active ingredient. Thus, the formulation compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders. The compositions may contain anywhere from about 0.1% to about 99.9% active ingredients, depending upon the selected dose and dosage form.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents;

preserving agents such as methyl- and propylhydroxybenzoates; sweetening agents; and flavoring agents. The compositions can be formulated so as to provide quick, sustained or delayed release of the active ingredient after administration to the patient by employing procedures known in the art. It is appreciated that the carriers, diluents, and excipients used to prepare the compositions described herein are advantageously GRAS (generally regarded as safe) compounds.

Examples of emulsifying agents are naturally occurring gums (e.g., gum acacia or gum tragacanth) and naturally occurring phosphatides (e.g., soybean lecithin and sorbitan monooleate derivatives). Examples of antioxidants are butylated hydroxy anisole (BHA), ascorbic acid and derivatives thereof, tocopherol and derivatives thereof, butylated hydroxy anisole, and cysteine. Examples of preservatives are parabens, such as methyl or propyl p-hydroxybenzoate, and benzalkonium chloride. Examples of humectants are glycerin, propylene glycol, sorbitol, and urea. Examples of penetration enhancers are propylene glycol, DMSO, triethanolamine, N,N-dimethylacetamide, N,N-dimethylformamide, 2-pyrrolidone and derivatives thereof, tetrahydrofurfuryl alcohol, and AZONE. Examples of chelating agents are sodium EDTA, citric acid, and phosphoric acid. Examples of gel forming agents are CARBOPOL, cellulose derivatives, bentonite, alginates, gelatin and polyvinylpyrrolidone. Examples of ointment bases are beeswax, paraffin, cetyl palmitate, vegetable oils, sorbitan esters of fatty acids (Span), polyethylene glycols, and condensation products between sorbitan esters of fatty acids and ethylene oxide (e.g., polyoxyethylene sorbitan monooleate (TWEEN)).

METHODS AND EXAMPLES

Syn-Syn-Syn (SSS) tris-THF Alcohol

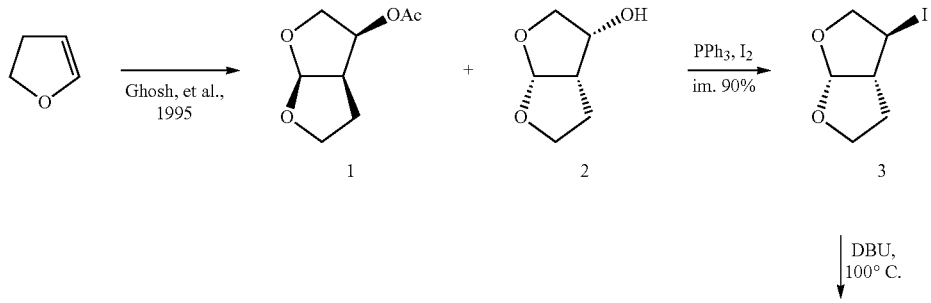

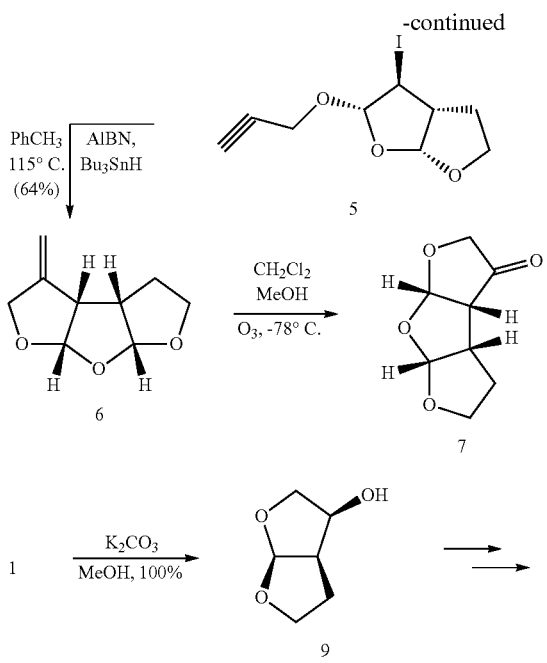
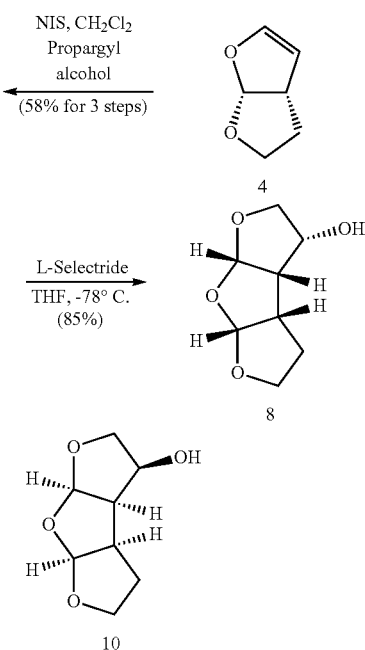

Synthesis of Syn-Syn-Syn (SSS)-type tris-THF Alcohol

The fused Syn-Syn-Syn (SSS)-type tris-tetrahydrofuran (tris-THF) ligands 8 and 10 were synthesized as outlined in Scheme 1. The (3R, 3aS, 6aR)-3-hydroxyhexahydrofuro[2,3-b]furan (bis-THF alcohol) 2 was prepared according to the known procedure. The bis-THF alcohol 2 was converted to the corresponding iodide 3 in 90% yield with triphenylphosphine and iodine, which undergoes β-elimination to give the cyclic vinyl ether 4. Compound 4 is very volatile and was directly used for the next reaction in the presence of solvent. Accordingly, cyclic vinyl ether 4 was treated with NIS and propargyl alcohol in CH$_2$Cl$_2$ at 0° C. to afford iodide 5 in 58% yield over three steps. Radical cyclization of 5 initiated by AIBN afforded the corresponding tris-THF alkene 6 which was cleaved by ozonolysis to afford the tris-THF ketone 7 in 68% yield over two steps. The syn-syn-syn configuration of 7 was confirmed by NOESY and X-ray crystal structure (Figure 1). Reduction of ketone 7 with L-Selectride generated the alcohol 8 in 85% yield as a single isomer. Following the same procedure, the enantiomer 10 was prepared using 1 as the starting material.

Synthesis of Syn-Anti-Syn (SAS)-type tris-THF alcohol

Commercially available 2,3-dihydrofuran was treated with ethyl diazoacetate and anhydrous CuSO$_4$ at reflux to provide the tetrahydrafuranyl cyclopropanyl ester 11 (4:1 dr) as shown in Scheme 2. LAH reduction of the resulting ester gave the corresponding primary alcohol 12 in quantitative yield. Oxidation of primary alcohol 12 with IBX generated the corresponding aldehyde, which underwent an in-situ arrangement to afford the racemic cyclic vinyl ether 4. With this route, racemate alkene 4 could be obtained from 2,3-dihydrofuran in three steps in 35% yield. In comparison, it needs six steps to get the same alkene 4 described in Scheme 1.

Scheme 2. Synthesis of bis-THF Alkene 4 from Cyclopropyl Ester 11.

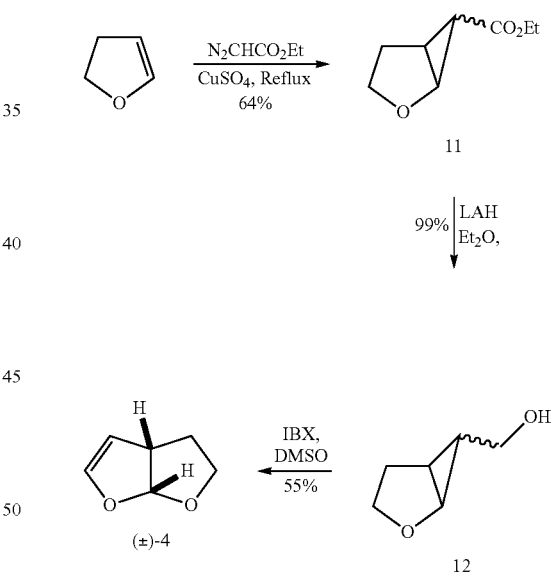

The synthetic route for tris-THF with SAS ring fusion is depicted in Scheme 3. Alkene 4 was exposed to freshly prepared acetone-free DMDO in CH$_2$Cl$_2$ at −78° C. to afford the corresponding epoxide, which was opened by methanol/sodium methoxide to provide the alcohol 13 in 96% yield. Addition of a catalytic amount (10%) of sodium methoxide is critical for this reaction. The stereochemistry was confirmed by $^1$H-NMR coupling constant comparison and nOe analysis. Oxidation of the alcohol 13 with Des s-Martin reagent generated the corresponding ketone. L-Selectride reduction of the ketone gave the 3-OH inverted alcohol 14 exclusively in 58% yield over two steps.

Scheme 3. Synthesis of SAS-type tris-THF alcohol (±)-19.

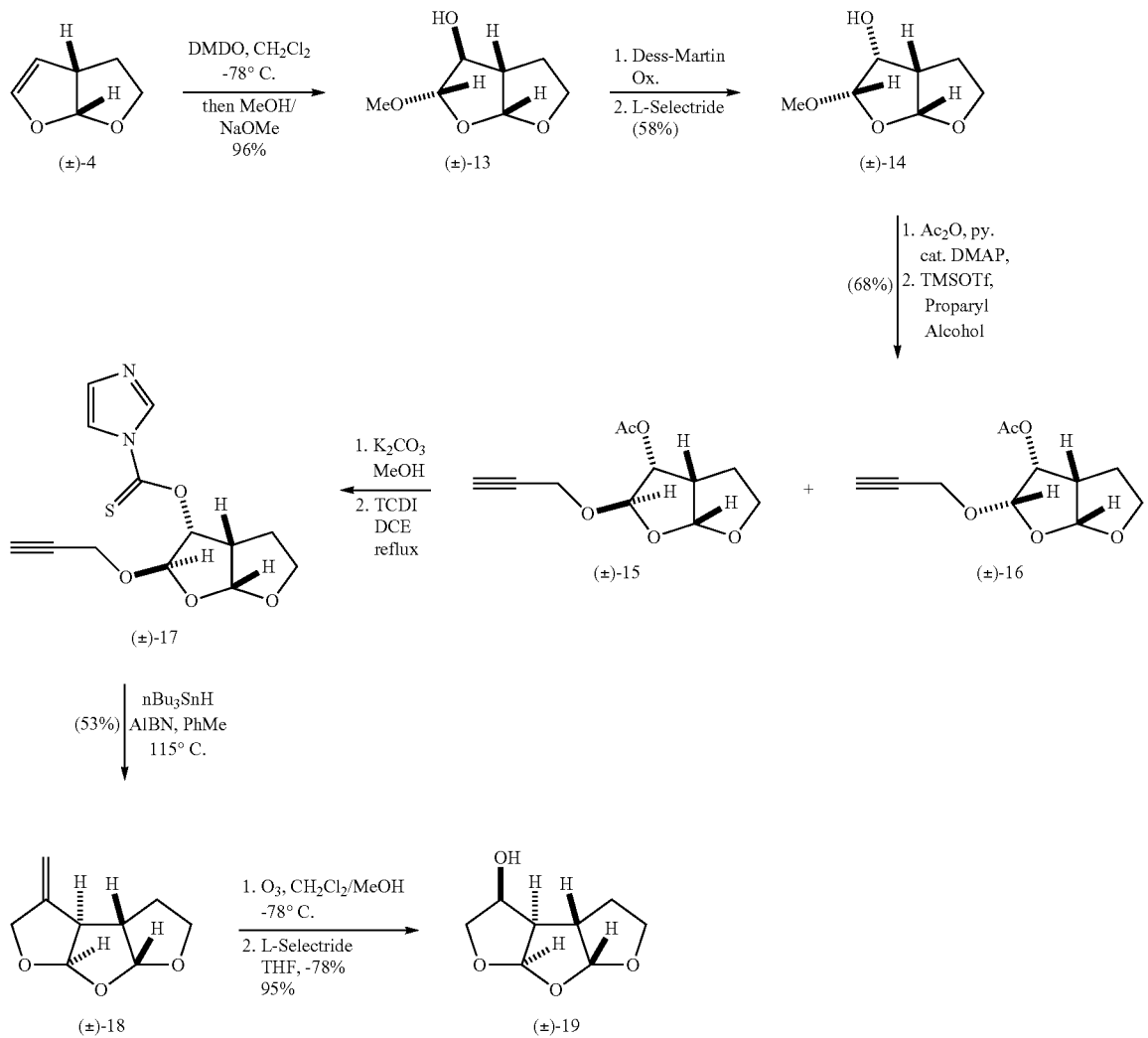

The inversion of the stereochemistry was easily confirmed by $^1$H-NMR and nOe analysis. Acylation of alcohol 14 and subsequent glycosylation with propargyl alcohol exchange promoted by TMSOTf provided the corresponding acetals 15 and 16 in 4:1 ratio as an inseparable mixture. After removal of the acetyl protecting group, the two diastereomers were readily separated by flash chromatography to provide the corresponding alcohol. Conversion of the resulting alcohol to tricyclic alkene 18 was carried out in a two step sequence: 1) conversion of the hydroxyl group to the thiocarbonyl derivative using 1,1'-thiocarbonyldiimidazole under neutral conditions to the thiocarbonyl derivative 17 in 95% yield) radical cyclization with tri-n-butyltin hydride in refluxing toluene initiated by AIBN to afford tricyclic alkene 18 in 75% yield. Cleavage of the double bond of the resulting alkene 18 with a stream of $O_3$ in $CH_2Cl_2/CH_3OH$ at −78° C. generated the corresponding tricyclic ketone in 89% yield. L-Selectride reduction of the resulting ketone gave the racemate SAS-type tris-THF alcohol (±)-19 exclusively in 95% yield.

Scheme 4. Kinetic Resolution of tris-THF alcohol (±)-19 with Lipase 30.

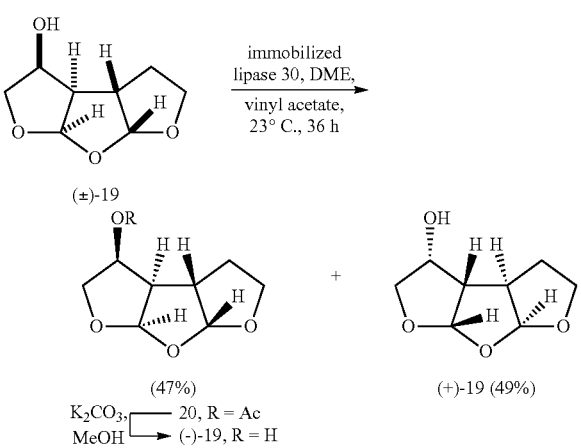

With the racemate SAS-type tris-THF alcohol (±)-19 in hand, herein described are procedures to make enantiopure tris-THF alcohol (Scheme 3.7). Based on the strategy of preparing bis-THF alcohol, an enzyme kinetic resolution was used to separate two enantiomers. Thus, the racemate compound (±)-19 was resolved with immobilized lipase 30, vinyl acetate and DME for 36 h to afford free alcohol (+)-19 in 49% yield and acylated product 20 in 47% yield. Ester 20 was hydrolyzed with $K_2CO_3$ and methanol to get the other SAS-type tris-THF enantiomer (−)-19 in 100% yield.

Synthesis THF-Cy-THF P2 Ligand 28 and 30

The synthesis of ligand 28 is depicted in Scheme 3.8. Enantiopure cyclopentenyl alcohol 22 was prepared according to a previously reported procedure. TBS protection and hydrolysis of acetate 22 afforded the alcohol 23 in quantitative yield. It was converted to the corresponding bromo acetal utilizing ethyl vinyl ether and NBS in $CH_2Cl_2$ followed by removal of TBS to give alcohol 24 in 85% yield over two steps. Treatment of alcohol 24 with NaH and propargyl bromide in the presence of TBAI gave the cyclization precursor 25 in 90% yield. The cascade cyclization using tri-n-butyltin hydride in refluxing toluene initiated by AIBN generated the tricyclic alkene 26 in 79% yield. Acetal reduction with trifluoroboron diethyl etherate and triethylsilane provided the alkene 27 in 76% yield. Cleavage of the double bond by ozonolysis at −78° C. followed by $NaBH_4$ reduction at −15° C. in a single operation afforded the P2 ligand 28 in 85% yield.

Treatment of alcohol 23 under Mitsunobu condition and the subsequent hydrolysis resulted in the corresponding inverted alcohol 29 in 90% yield over 2 steps. Following the same procedure described earlier, ligand 30 was synthesized.

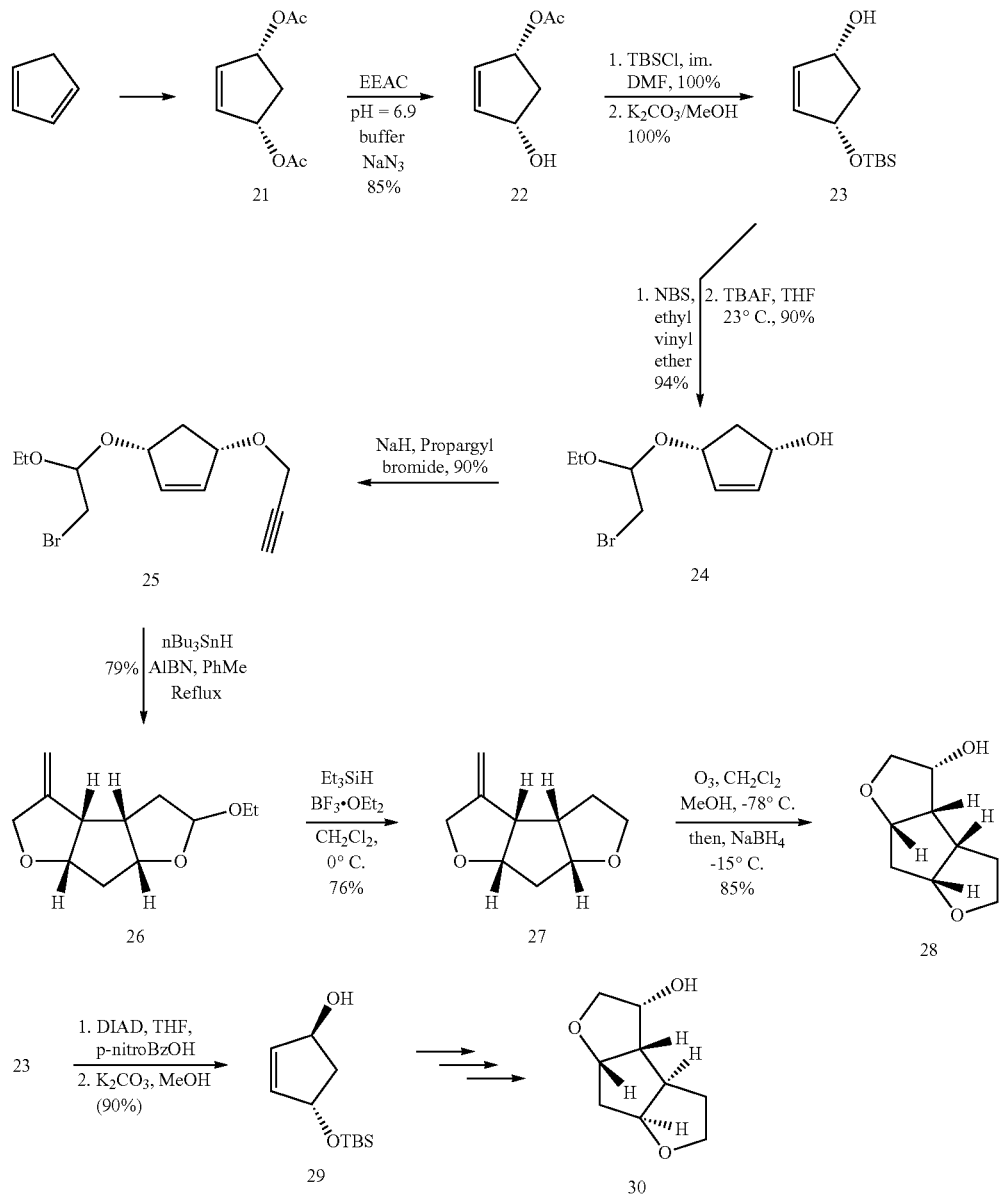

Scheme 5. Synthesis of THF-Cp-THF Alcohol 28 and 30.

Synthesis of Inhibitor 31-36

The syntheses of inhibitors 31-36 are outlined in Scheme 6. The ligand alcohols were converted to the corresponding p-nitrophenyl carbonate 37a-f utilizing p-nitrophenyl chloroformate and N-methyl morpholine in various solvents. Commercially available epoxide 38 was opened with isobutylamine in 2-propanol at 65° C. for 3 h. The crude product was subjected to sulfonation to afford isostere 39 in quantitative yield according to a previously reported procedure. Treatment of isostere 39 with trifluoroacetic acid followed by coupling of the amine with the corresponding carbonate 37a-f to gives inhibitors 31-36.

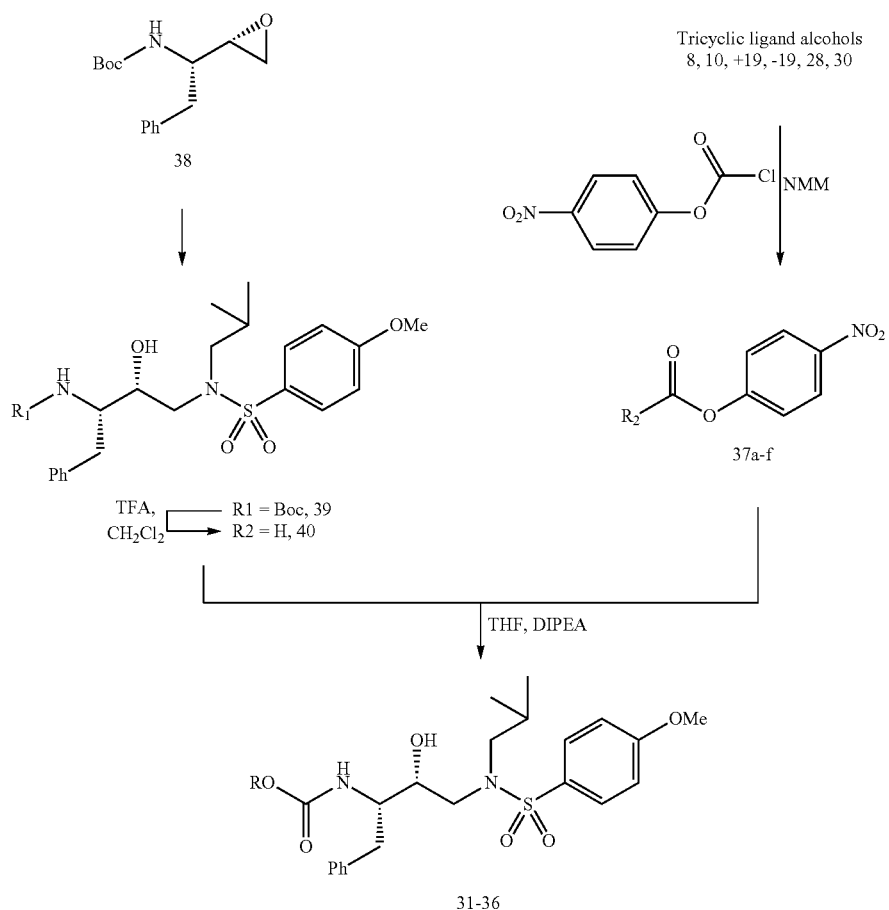

Scheme 6. Synthesis of Inhibitors 31-36.

TABLE 1

Enzymatic Inhibitory Activity of Compounds 31-36, and Antiviral activity of Selected Inhibitors against HIV-1$_{LAI}$

| Entry | Inhibitor | $K_i$ | $IC_{50}$ |
|---|---|---|---|
| 1 | (structure 31) | | + |

TABLE 1-continued
| | | | |
|---|---|---|---|
| 2 | 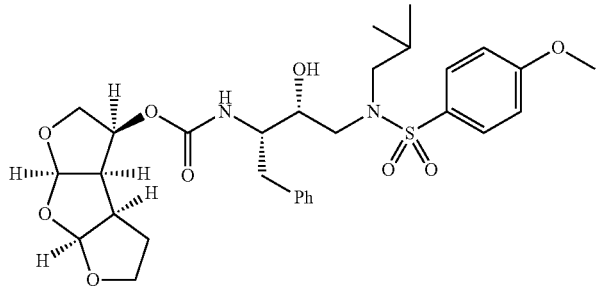
32 | +++ | |
| 3 | 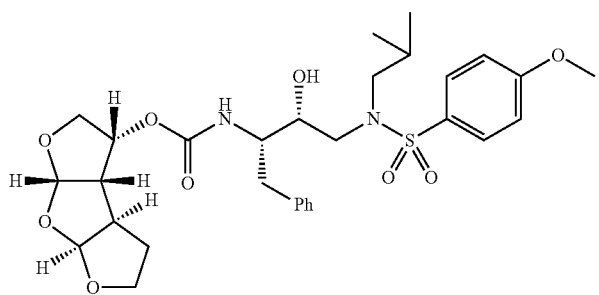
33 | +++ | +++ |
| 4 | 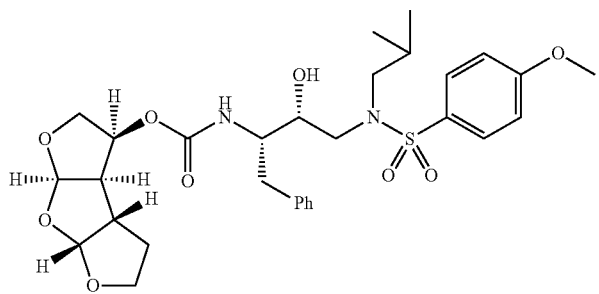
34 | + | + |
| 5 | 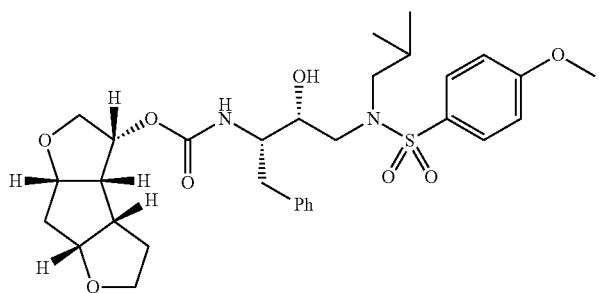
35 | + | + |

TABLE 1-continued

| # | Inhibitor Structure | $K_i$ | |
|---|---|---|---|
| 6 | | + | − |
| 7 | | ++ | |
| 8 | | +++ | +++ |

| | Inhibitor Structure | $K_i$ |
|---|---|---|
| 9 | | +++ |
| 10 | | +++ |

TABLE 1-continued
| 11 | 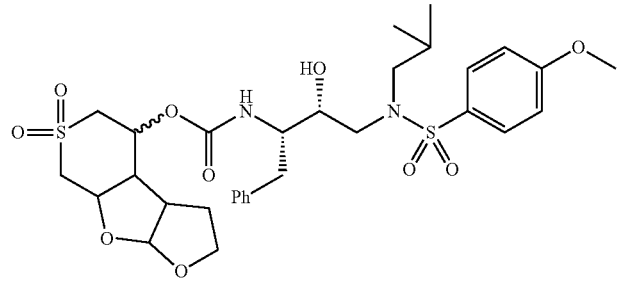 [SMILES: COc1ccc(S(=O)(=O)N(CC(C)C)C[C@@H](O)[C@H](Cc2ccccc2)NC(=O)OC2CS(=O)(=O)CC3OC4OCCC4C23)cc1] | ++ |
| 12 | 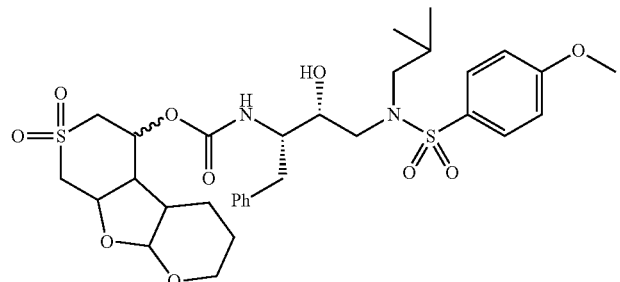 | − |
| 13 | 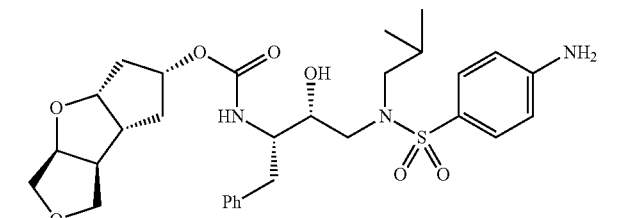 | +++ |
| 14 | 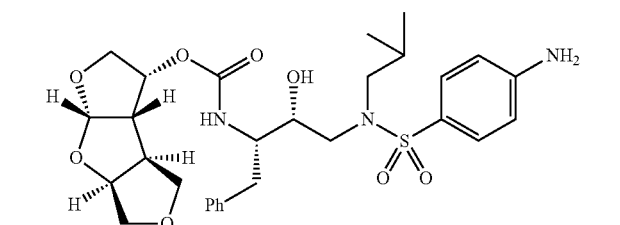 | +++ |
| 15 | 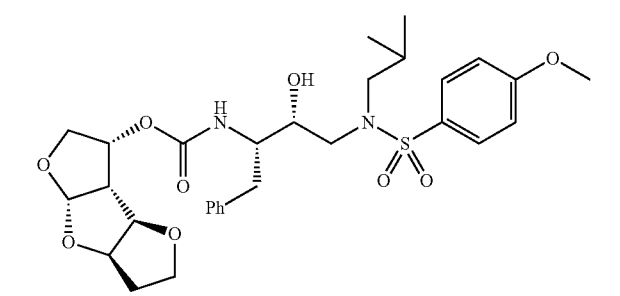 [SMILES: COc1ccc(S(=O)(=O)N(CC(C)C)C[C@@H](O)[C@H](Cc2ccccc2)NC(=O)O[C@H]2CO[C@H]3O[C@@H]4CCO[C@@H]4[C@H]32)cc1] | +++ |
| 16 | 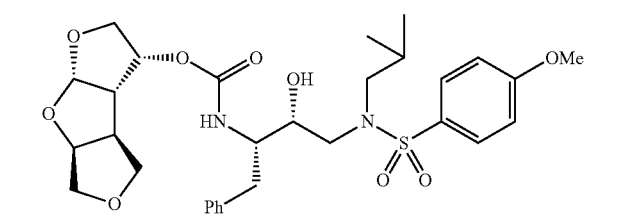 [SMILES: COc1ccc(S(=O)(=O)N(CC(C)C)C[C@@H](O)[C@H](Cc2ccccc2)NC(=O)O[C@H]2CO[C@H]3O[C@@H]4COC[C@@H]4[C@H]32)cc1] | +++ |

TABLE 1-continued

| | | |
|---|---|---|
| 17 | 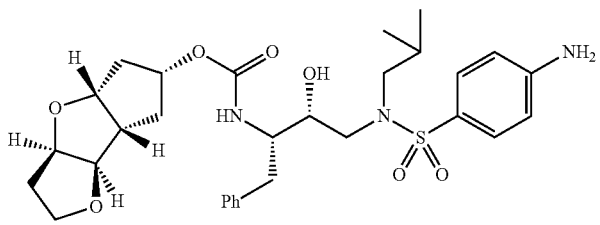 [SMILES: CC(C)CN(C[C@@H](O)[C@H](Cc1ccccc1)NC(=O)O[C@@H]1C[C@@H]2[C@H]3OCC[C@H]3O[C@@H]2C1)S(=O)(=O)c1ccc(N)cc1] | − |
| 18 | 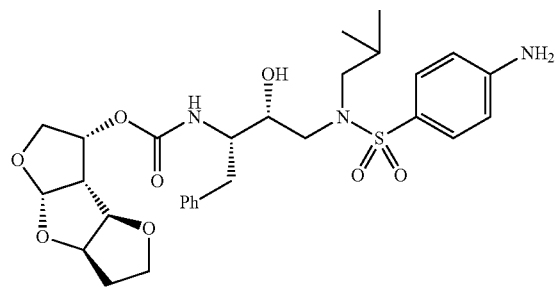 [SMILES: CC(C)CN(C[C@@H](O)[C@H](Cc1ccccc1)NC(=O)O[C@H]1CO[C@H]2O[C@@H]3CCO[C@@H]3[C@H]21)S(=O)(=O)c1ccc(N)cc1] | +++ |

Ki: >10 nM, −; <10 nM, +; <1 nM, ++; and <0.1 nM, +++
IC$_{50}$: >1 µM, −; <1 µM, +; <0.1 µM, ++; and <0.01 µM, +++

Resistance Profiles for Inhibitors 33, 34

Relative Antiviral activity of 33, and 34 against multi-drug resistant clinical isolates in PHA-PBMs

| Virus | (33) | (34) | APV (Amprenavir) | DRV (Darunavir) |
|---|---|---|---|---|
| HIV-1$_{ERS104pre}$ (wild-type: X4) | 1 | 1 | 1 | 1 |
| HIV-1$_{MDR/B}$ (X4) | 7 | 2 | 16 | 6 |
| HIV-1$_{MDR/C}$ (X4) | 2 | 1 | 11 | 2 |
| HIV-1$_{MDR/G}$ (X4) | 5 | 2 | 15 | 6 |
| HIV-1$_{MDR/TM}$ (X4) | 4 | 2 | 15 | 6 |
| HIV-1$_{MDR/MM}$ (R5) | 5 | 2 | 9 | 3 |
| HIV-1$_{MDR/JSL}$ (R5) | 5 | >2 | 13 | 5 |

The amino acid substitutions identified in the protease-encoding region of HIV-1$_{ERS104pre}$, HIV-1$_B$, HIV-1$_C$, HIV-1$_G$, HW-1$_{TM}$, HIV-1$_{MM}$, HIV-1$_{JSL}$ compared to the consensus type B sequence cited from the Los Alamos database include L63P; L10I, K14R, L33I, M36I, M46I, F53I, K55R, I62V, L63P, A71V, G73S, V82A, L90M, I93L; L10I, I15V, K20R, L24I, M36I, M46L, I54V, I62V, L63P, K70Q, V82A, L89M; L10I, V11I, T12E, I15V, L19I, R41K, M46L, L63P, A71T, V82A, L90M; L10I, K14R, R41K, M46L, I54V, L63P, A71V, V82A, L90M; I93L; L10I, K43T, M46L, I54V, L63P, A71V, V82A, L90M, Q92K; and L10I, L24I, I33F, E35D, M36I, N37S, M46L, I54V, R57K, I62V, L63P, A71V, G73S, V82A, respectively. HIV-1$_{ERS104pre}$ served as a source of wild-type HIV-1. The IC$_{50}$ values were determined by using PHA-PBMs as target cells and the inhibition of p24 Gag protein production by each drug was used as an endpoint. The numbers in parentheses represent the fold changes of IC$_{50}$ values for each isolate compared to the IC$_{50}$ values for wild-type HIV-1$_{ERS104pre}$. All assays were conducted in duplicate.

What is claimed is:

1. A compound selected from the group consisting of compounds of the formulas

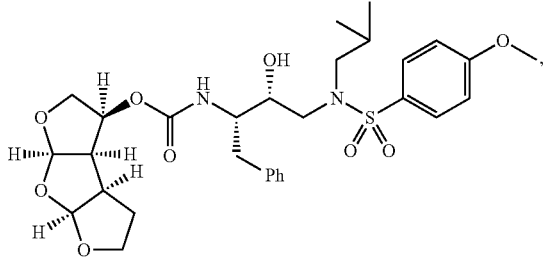

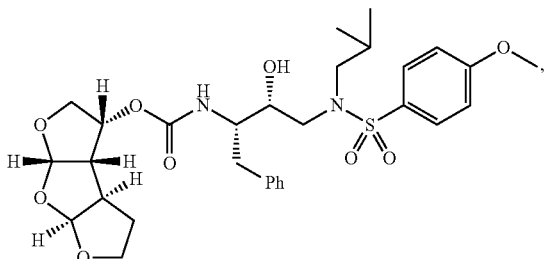

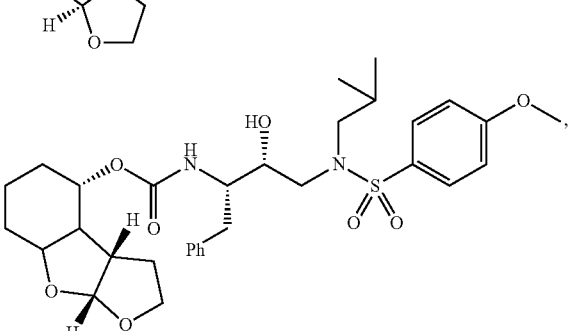

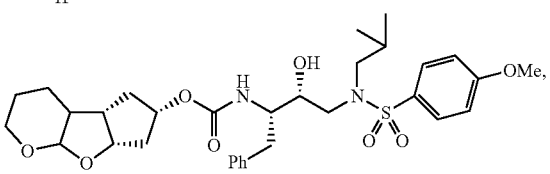

-continued

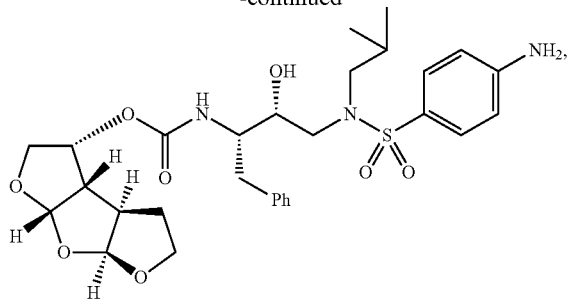

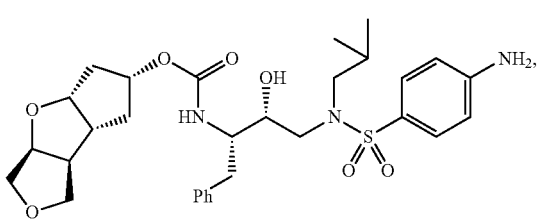

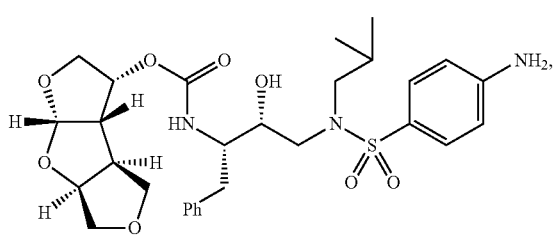

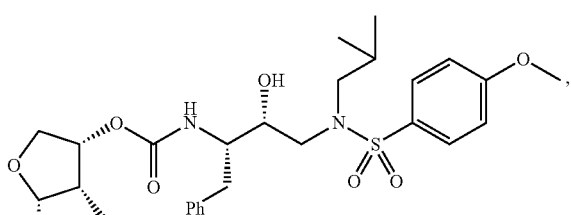

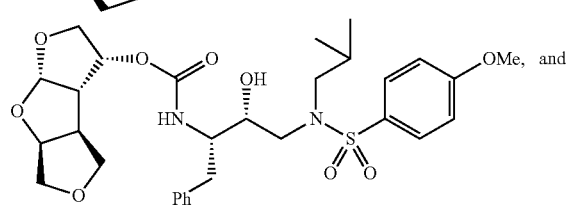

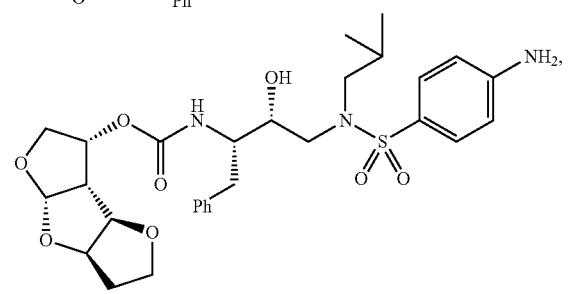

or a pharmaceutically acceptable salt thereof.

2. A compound of the formula

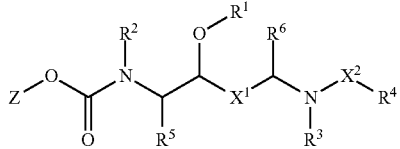

or a pharmaceutically acceptable salt thereof, wherein
$X^1$ is a bond and $R^6$ is hydrogen;
$X^2$ is $S(O)_2$, and $R^4$ is optionally substituted aryl;
$R^1$ and $R^2$ are each hydrogen;
$R^3$ is alkyl which is optionally substituted;
$R^5$ is optionally substituted arylalkyl;
Z is

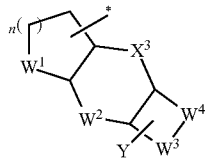

wherein * indicates the point of attachment; n is 1 or 2;
$W^1$ and $W^2$ are in each instance independently selected from the group consisting of optionally substituted methylene, oxygen, and amino;
$W^3$ and $W^4$ are in each instance independently selected from the group consisting of amino, oxygen, alkylene, and heteroalkylene, wherein at least one of $W^1$ or $W^2$ is oxygen, and wherein when one of $W^1$ or $W^2$ is optionally substituted methylene, at least one of $W^3$ or $W^4$ is oxygen, and wherein Z does not include a peroxide bond, a sulfenate bond, or a sulfenamide bond;
$X^3$ is a bond; and
Y is hydrogen.

3. The compound of claim 2 wherein Z is

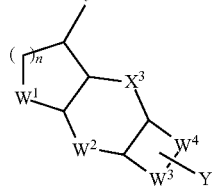

wherein * indicates the point of attachment.

4. The compound of claim 2 wherein Z is

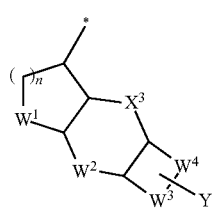

wherein $W^2$ is an oxygen; and * indicates the point of attachment.

5. The compound of claim 2 wherein Z is

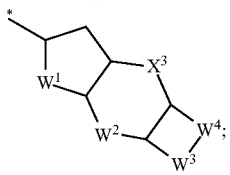

and W² is an oxygen.

6. The compound of claim 2 wherein R⁵ is phenylmethyl.

7. The compound of claim 2 wherein W³ is oxygen and W⁴ is optionally substituted ethylene or propylene.

8. The compound of claim 2 wherein n is 1.

9. The compound of claim 7 wherein W⁴ is optionally substituted ethylene.

10. The compound of claim 2 wherein Z is

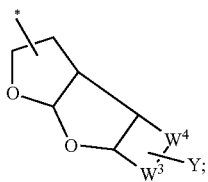

wherein W³ is optionally substituted methylene; and W4 is —CH₂O— or —OCH₂.

11. The compound of claim 2 wherein W¹, W², and W³ are oxygen.

12. A pharmaceutical composition comprising one or more compounds of claim 1 and further comprising one or more carriers, diluents, or excipients, or a combination thereof.

13. A method for treating a patient in need of relief from an HIV infection, the method comprising the step of administering to a patient in need of relief from the HIV infection a therapeutically effective amount of one or more compounds of claim 1 or pharmaceutical composition thereof.

14. The compound of claim 1 of formula

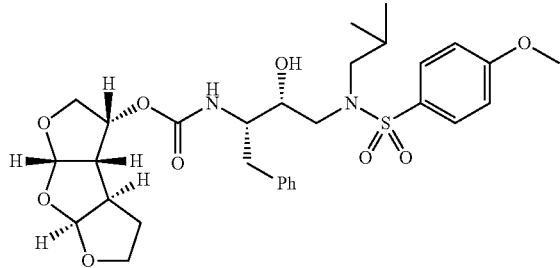 [SMILES: COc1ccc(S(=O)(=O)N(CC(C)C)C[C@@H](O)[C@H](Cc2ccccc2)NC(=O)O[C@H]2CO[C@H]3O[C@@H]4OCC[C@@H]4[C@H]32)cc1]

or a pharmaceutically acceptable salt thereof.

15. A method for treating a patient in need of relief from an HIV infection, the method comprising the step of administering to a patient in need of relief from the HIV infection a therapeutically effective amount of the compound of claim 14 or pharmaceutical composition thereof.

16. The compound of claim 1 of formula

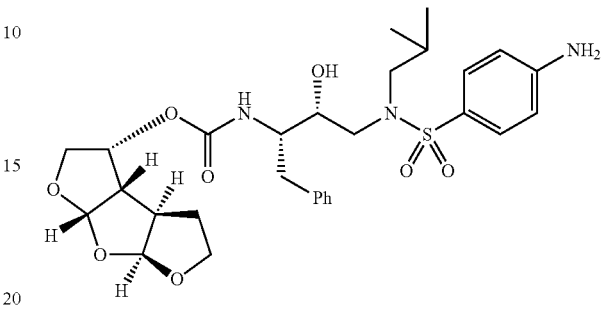

or a pharmaceutically acceptable salt thereof.

17. A method for treating a patient in need of relief from an HIV infection, the method comprising the step of administering to a patient in need of relief from the HIV infection a therapeutically effective amount of the compound of claim 16 or pharmaceutical composition thereof.

18. The compound of claim 1 of formula

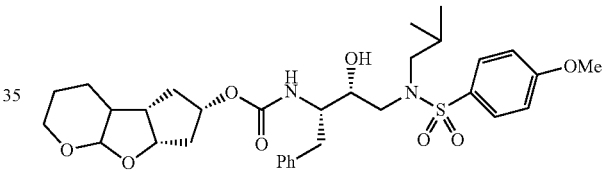

or a pharmaceutically acceptable salt thereof.

19. A method for treating a patient in need of relief from an HIV infection, the method comprising the step of administering to a patient in need of relief from the HIV infection a therapeutically effective amount of the compound of claim 18 or pharmaceutical composition thereof.

20. A method for treating a patient in need of relief from an HIV infection, the method comprising the step of administering to a patient in need of relief from the HIV infection a therapeutically effective amount of the compound of claim 2 or pharmaceutical composition thereof.

* * * * *